United States Patent
Sandoval, Jr. et al.

(10) Patent No.: US 10,571,397 B2
(45) Date of Patent: *Feb. 25, 2020

(54) COMPOSITIONS COMPRISING A BUFFERING SOLUTION AND AN ANIONIC SURFACTANT AND METHODS FOR OPTIMIZING THE DETECTION OF FLUORESCENT SIGNAL FROM BIOMARKERS

(71) Applicant: PHARMACOPHOTONICS, INC., Indianapolis, IN (US)

(72) Inventors: Ruben Sandoval, Jr., Indianapolis, IN (US); Erinn Reilly, Indianapolis, IN (US); Daniel Meier, Indianapolis, IN (US)

(73) Assignee: PHARMACOPHOTONICS, INC., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/116,248

(22) Filed: Aug. 29, 2018

(65) Prior Publication Data

US 2019/0064068 A1 Feb. 28, 2019

Related U.S. Application Data

(63) Continuation of application No. 15/031,452, filed as application No. PCT/US2014/062170 on Oct. 24, 2014, now Pat. No. 10,082,465.

(Continued)

(51) Int. Cl.
*G01N 21/64* (2006.01)
*A61K 49/00* (2006.01)
*A61M 5/00* (2006.01)

(52) U.S. Cl.
CPC ..... *G01N 21/6428* (2013.01); *A61K 49/0041* (2013.01); *A61K 49/0054* (2013.01);
(Continued)

(58) Field of Classification Search
CPC ............... A61K 49/0041; A61M 5/007; G01N 2021/6439; G01N 21/6428; G01N 33/533; G01N 33/582
(Continued)

(56) References Cited

U.S. PATENT DOCUMENTS

| 4,816,419 A | 3/1989 | Hafman |
| 7,129,093 B2 * | 10/2006 | McCleskey .......... G01N 21/643 436/79 |

(Continued)

FOREIGN PATENT DOCUMENTS

| WO | 2009140026 A2 | 11/2009 |
| WO | 2010127136 A2 | 11/2010 |

OTHER PUBLICATIONS

Du et al. "Effect of anionic surfactants with different structure on the fluorescent properties of the CPPO-H2O2-Rhodamine B system." Mater. Sci. Forum. 663-665(2010):207-210.

(Continued)

*Primary Examiner* — Que Tan Le
(74) *Attorney, Agent, or Firm* — Burns & Levinson, LLP; Bruce D. Jobse

(57) ABSTRACT

Compositions and methods for increasing fluorescent signals generated by biomarkers are described. This serves to increase the accuracy of results when the biomarkers are used for the detection and diagnosis of physiological conditions, such as organ function and plasma volume.

17 Claims, 6 Drawing Sheets

Related U.S. Application Data

(60) Provisional application No. 61/894,963, filed on Oct. 24, 2013.

(52) U.S. Cl.
CPC ..... *A61M 5/007* (2013.01); *G01N 2021/6417* (2013.01); *G01N 2021/6439* (2013.01); *G01N 2201/13* (2013.01)

(58) Field of Classification Search
USPC ...................................................... 250/559.4
See application file for complete search history.

(56) References Cited

U.S. PATENT DOCUMENTS

| | | |
|---|---|---|
| 2011/0201940 A1 | 8/2011 | Wang et al. |
| 2012/0276014 A1 | 11/2012 | Molitoris et al. |
| 2013/0096309 A1 | 4/2013 | Bremberg et al. |
| 2013/0230876 A1 | 9/2013 | Roscoe et al. |
| 2014/0193343 A1 | 7/2014 | Molitoris et al. |
| 2014/0301952 A1 | 10/2014 | Molitoris et al. |
| 2014/0369936 A1 | 12/2014 | Meier et al. |
| 2016/0026604 A1 | 1/2016 | Pandit et al. |

OTHER PUBLICATIONS

Mather et al. "Detection of DNA Sequence with Enhanced Sensitivity and Higher FRET Efficiency Using a Light Emitting Polymer, Peptide Nucleic Acid Probe and Anionic Surfactant System." J. Biomater. Sci. 22(2011):379-387.

\* cited by examiner

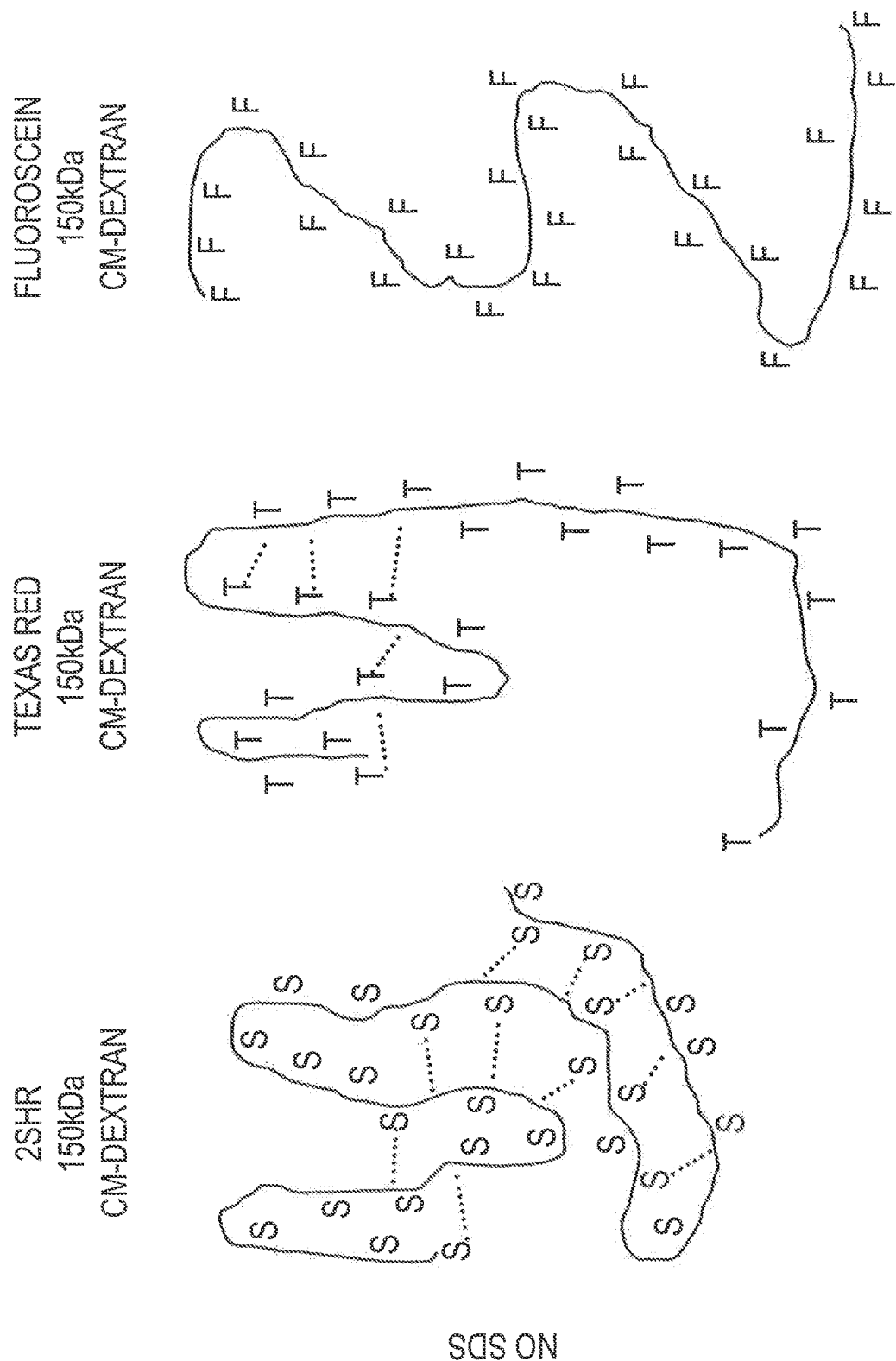

COMPOSITIONS COMPRISING A BUFFERING SOLUTION AND AN ANIONIC SURFACTANT AND METHODS FOR OPTIMIZING THE DETECTION OF FLUORESCENT SIGNAL FROM BIOMARKERS

FIELD OF THE INVENTION

The present invention relates generally to compositions and methods for optimizing the detection of fluorescent signals generated by fluorescent markers introduced into the vascular system of a subject.

BACKGROUND OF THE INVENTION

Fluorescent spectrophotometric systems used for medical diagnostic analysis conventionally include a light source for exciting a fluorescent marker in a sample of biological fluid, such as a blood plasma sample. The light source excites the marker which, in turn, emits a fluorescent signal. The fluorescent signal is received by a light detector which measures the intensity of the emitted signal as a measure of the concentration of the biological parameter of interest. Such parameters can include, for example, plasma volume, glomerular filtration rate (GFR), and hematocrit. The spectrophotometric systems also include a means for storing spectrophotometric data, such as a digital memory storage device, a means for processing the spectrophotometric data, such as a digital computation processor, and an output for the processed data, such as a digital display. Typical fluorescent spectrophotometric systems used for the analysis of biomarkers, as well as methods for measuring biometric indicators, are disclosed in U.S. patent application Ser. Nos. 12/425,827 and 12/946,471, and PCT Patent Application Nos. PCT/US09/40994 and PCT/US10/32997.

In practice, a bolus injection containing one or more fluorescent markers, such as a dynamic marker and a static marker, is administered to the animal, and the change in concentration of the marker(s) is monitored over time to create an output data set. The data set can then be used to calculate the biological parameter of interest using mathematical models.

The accurate detection and measurement of the fluorescent marker is critical to the proper functioning of spectrophotometric analytical systems. Typically, a blood sample is taken from the patient and combined with a buffering solution and surfactant to form a medium for analysis. A light source is used to activate the fluorescent marker in the medium, and to generate fluorescent signals which are detected by a light detector. It has been found that in practice certain surfactants used in the medium can actually cause the suppression of the fluorescent signal, which can lead to errors in detection and false results supplied to the clinician.

Accordingly, it is a primary objective of the present invention to provide a composition and method for enhanced fluorescent signal detection from fluorescent markers used for the diagnosis of biological function and organ status in patients.

The present invention is intended to solve the problems discussed above, and to provide advantages not provided by prior techniques. A full discussion of the features and advantages of the present invention is deferred to the following detailed description, which also proceeds with reference to the accompanying drawings.

SUMMARY OF THE INVENTION

The present invention relates to compositions and methods for the enhanced detection of signals generated by biological markers used for the diagnosis and detection of the physiological condition or disease state of an animal. Specifically, the biological markers of the present invention are fluorescent molecules conjugated to macromolecules which are administered to a patient for the purpose of clinical diagnosis. According to the invention, a sample of a biological fluid is periodically obtained from a patient, and the amount of the biomarker in the sample is quantified in a media formed from the sample, a buffering solution, and a surfactant. The media is subjected to a light source to activate the fluorescent signal, and the signal is detected using a light detector. The data collected is analyzed in a spectrophotometric analyzer and computer. Preferably the animal is a human patient.

The composition is for increasing fluorescent signals generated by a biological marker used for the diagnosis of a physiological condition or disease or for monitoring a biometric parameter in an animal. The composition includes, in admixture, a buffering solution, a biological marker comprising at least one fluorescent molecule, and an anionic surfactant.

In various embodiments of the composition, the surfactant is an anionic surfactant, preferably SDS, and the biomarker is an anionic fluorescently-labeled dextran, preferably a fluorescently-labeled carboxy methyl dextran having a molecular weight of from about 70 kDA to about 500 kDA. More preferably, the dextran is conjugated (i.e. covalently bound) to one or more slightly cationically charged fluorophores. Preferably the fluorophore is 2 sulfhydrorhodamine. The buffering solution is a biological buffer, preferably PBS.

In various embodiments of the composition, the physiological condition being measured is either organ function, such as kidney function, or plasma volume. The measurement of kidney function can be obtained by measuring glomerular filtration rate.

The method for analyzing a biometric parameter in an animal includes the steps of administering a fluorescent molecule (i.e. a biomarker) to the vascular system of an animal; permitting the fluorescent molecule to reach equilibrium; obtaining periodic samples of blood from the animal; isolating a plasma sample from the blood; forming a medium containing the blood plasma sample, a buffering solution and an anionic surfactant; detecting the fluorescent signal(s) generated by the fluorescent molecule(s); measuring and quantifying the fluorescent signals; and comparing the quantity of the fluorescent signal(s) to the quantity from a control sample for a biometric parameter of the organ or tissue of the animal.

In various embodiments of the method for analyzing a biometric parameter, the biomarker is administered to an animal by intravenous injection, and the animal is a human patient. Preferably, the surfactant is an anionic surfactant (e.g. SDS), and the biomarker is an anionic fluorescently-labeled dextran, preferably a fluorescently-labeled carboxy methyl dextran having a molecular weight of from about 70 kDA to about 500 kDA. More preferably, the dextran is conjugated to one or more slightly cationically charged fluorophores, most preferably 2 sulfhydrorhodamine.

In still further embodiments of the method for analyzing a biometric parameter, blood samples are obtained from a patient at intervals ranging from 10 to 60 minutes, preferably 10 to 20 minutes, until sufficient data is obtained to permit a definitive correlation between organ function or plasma volume, and the fluorescent emission levels.

In various embodiments of the method for analyzing a biometric parameter, the buffering solution is PBS, and the biometric parameter is kidney function or plasma volume.

More specifically, the biometric parameter of kidney function is glomerular filtration rate.

The method for increasing fluorescent signal of a biological marker includes providing a biological sample containing a biological marker wherein the biological marker comprises at least one fluorescent molecule; and adding a buffer solution and an anionic surfactant to said sample.

In various embodiments of the method for increasing fluorescent signal of a biological marker, the biological sample is plasma and the biological marker is fluorescently-labeled anionic dextran. Preferably, the anionic dextran is a carboxy methyl dextran having a molecular weight in the range of from about 70 kDa to about 500 kDa, preferably about 150 kDa. The anionic dextran is conjugated to one or more cationically charged fluorophores, preferably fluorophore is 2 sulfhydrorhodamine (2SHR).

In further embodiments of the method for increasing fluorescent signal of a biological marker the anionic surfactant is sodium dodecyl sulfate (SDS) and the buffering solution is PBS. Preferably, the signal is increased at least about 2-fold as compared to signal in the absence of anionic surfactant.

Other features and advantages of the present novel technology will be apparent from the following description.

BRIEF DESCRIPTION OF THE DRAWINGS

To understand the present invention, it will now be described by way of example with reference to the accompanying drawings in which:

FIGS. 4A, 4B, 4C, 4D, 4E, and 4F are schematic representations of the effect of SDS on the ionic interaction of the anionic carboxy methyl groups in a 150 kDa dextran conjugated to TR, FITC and 2SHR, respectively.

DETAILED DESCRIPTION

Figure 1:
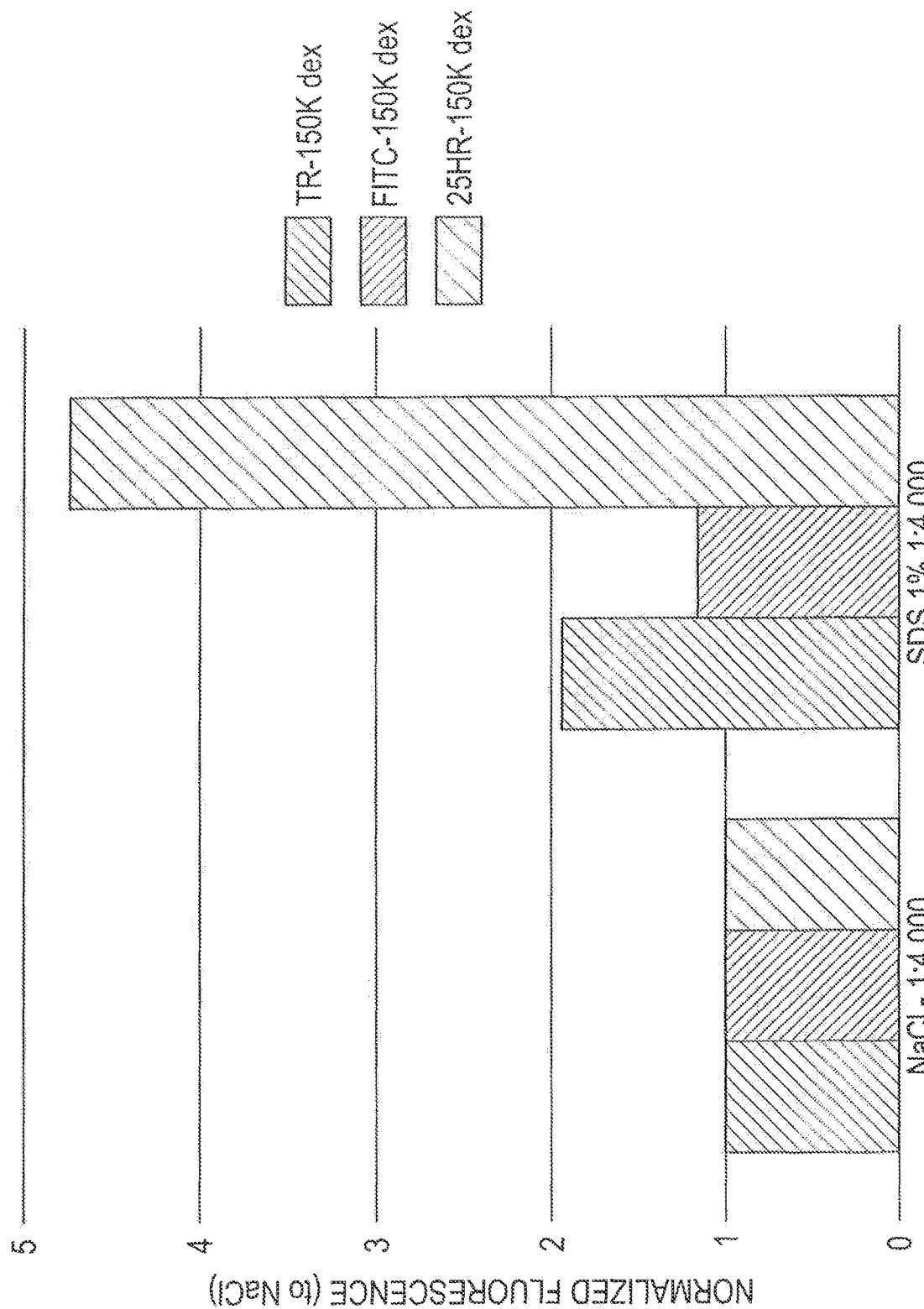
FIG. 1 is a bar graph showing the results of the addition of sodium dodecyl sulfate (SDS) to a medium for the detection of fluorescent signals using a 150 kDa carboxy methyl dextran conjugated to Texas Red (TR), 5-Amino Fluorescein (FITC), and 2-SulfhydroRhodamine (2SHR), respectively.

For the purposes of promoting an understanding of the principles of the invention, reference will be made to the embodiments illustrated in the drawings and specific language will be used to describe the same. It will nevertheless be understood that these embodiments constitute no limitation as to the scope of the invention, with such alterations and further modifications in the illustrated device, and such further applications of the principles of the technology as illustrated therein, being contemplated as would normally occur to one skilled in the art to which the technology relates.

The present invention relates to compositions and methods for optimizing the fluorescent signals generated by biological markers introduced into an animal in order to determine the physiological condition of the animal. In particular, the biomarkers of the invention comprise at least one fluorescent molecule conjugated to a macromolecule to form a conjugation product via covalent bonding. The biomarkers are introduced into an animal, such as a human subject, and allowed to reach equilibrium in the vascular system of the animal. Once equilibrium is achieved, biological samples, such as blood samples, are taken from the animal at periodic intervals. The plasma samples are then analyzed in a medium formed from the plasma sample, a buffering solution and an anionic surfactant. The analysis is conducted using a light source to activate the fluorescent molecule on the biomarker, and a light detector is used to measure and quantify the intensity of the fluorescent signal generated by the activated molecule. Biometric parameters, such as organ function or plasma volume, can be determined by comparing the values obtained from the samples of the subject with samples from a known source. This is information is then supplied to a clinician for evaluation and appropriate response.

As used herein, the term "biological marker" or "biomarker" is intended to denote a molecular entity designed to be introduced into the vascular system of an animal, preferably a human subject, primarily to measure the function of an organ or vasculature of the animal. It is a biocompatible molecule formed as the conjugation product of a fluorescent molecule or dye and a macromolecule.

The macromolecules of the invention typically comprise biopolymers, such as dextrans of various molecular weights. It has been found that the larger dextrans, i.e. dextrans with molecular weights in the range of from about 70 kDa to about 500 kDa, are particularly suitable for measuring plasma volume. Preferably, the dextrans of the invention are anionic carboxy methyl dextrans having a molecular weight of about 150 kDa. These molecules are biocompatible and can be used as injectates in humans.

The macromolecules of the invention are conjugated to fluorescent molecules, typically rhodamine derivatives which can be mono-functional or multi-functional. Typical fluorescent molecules include Texas Red (sulforhodamine 101, also TR), 5-Amino Fluorescein (FITC), and 2-SulhydroRhodamine (2SHR). The fluorescent molecules typically have various net charge states. For instance, TR is known to be a neutrally charged fluorophore, FITC is an anionically charged fluorophore, and 2SHR is a cationically charged fluorophore.

It has been found that when the medium for analysis is formed using conventional surfactants, or no surfactant, measurement errors of up to 30% or more occur. It will be readily appreciated by those skilled in the art that measurement errors of this magnitude can render test results essentially meaningless.

It is believed that such errors are due to the formation of weak ionic bonds between the fluorophore and the conjugated dextran. These bonds are particularly evident when the fluorophore has a net cationic charge and the dextran has an anionic charge, such as when a 2SHR (cationic charge) is conjugated to a carboxy methyl dextran (net anionic charge). It is postulated that in biomarkers of this type the weak ionic bond between the fluorophore and the dextran results in the formation of tertiary structures in the molecule that obstruct and obscure the fluorophore, reducing the fluorescent signal output, thereby resulting in erroneous measurements.

The invention is accordingly directed to an improved media for the detection of fluorescent signals emitted by fluorescent biomarkers. This is accomplished by optimizing the medium formed by the biomarker, buffer and surfactant. The surfactant typically used in the medium is replaced or supplemented with an anionic surfactant which is particularly effective when the fluorophor has a net positive charge and the dextran has a net negative charge, such as when 2SHR is conjugated to a 150 kDa carboxy methyl dextran.

The anionic surfactant of the invention can be selected from any of the well known anionic surfactants, including, but not limited to, sodium dodecyl sulfate, sodium 1-butanesulfonate, and sodium deoxycholate. Of these surfactants, sodium dodecyl sulfate is particularly preferred.

The buffering solution of the invention can be selected from any of well known biological buffers, including, but not limited to, PBS, TRIS, MOPS and HEPES. Of these buffering solutions, PBS is particularly preferred.

Turning to the figures, FIGS. 4A through 4F illustrate the effect of the use of sodium dodecyl sulfate as a surfactant on the structural conformation of a 150 kDa carboxy methyl dextran conjugated to 2SHR (FIGS. 4A and 4D), Texas Red (FIGS. 4B and 4E), and FITC (FIGS. 4C and 4F), respectively.

In particular, FIGS. 4A, 4B and 4C show the molecular structure of the indicated biomarkers in a medium without the addition of an anionic surfactant. FIG. 4A depicts a twisted or distorted molecular structure due to a series of ionic bonds formed between adjacent sections of the molecule, along the full length of the molecule. FIG. 4B shows a molecule which contains some distortion due to ionic bonding in some parts of the molecule, but not as substantially as in FIG. 4A. In FIG. 4C, by contrast, no such distortion is evident, indicating a lack of ionic bonding.

Figure 4F:
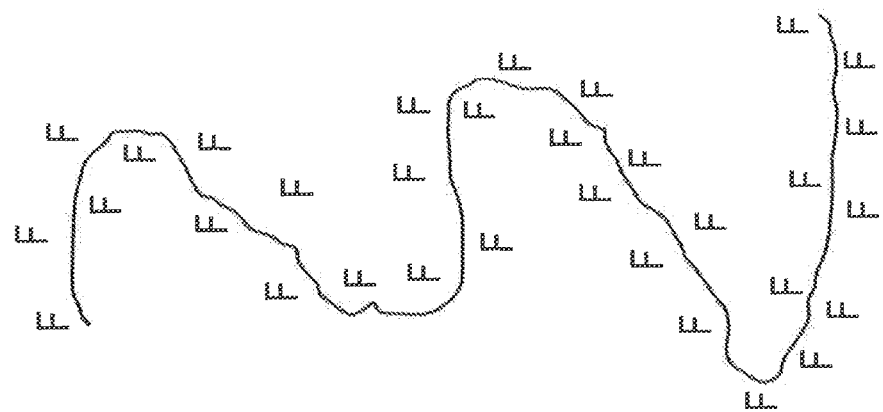
Figure 4E:
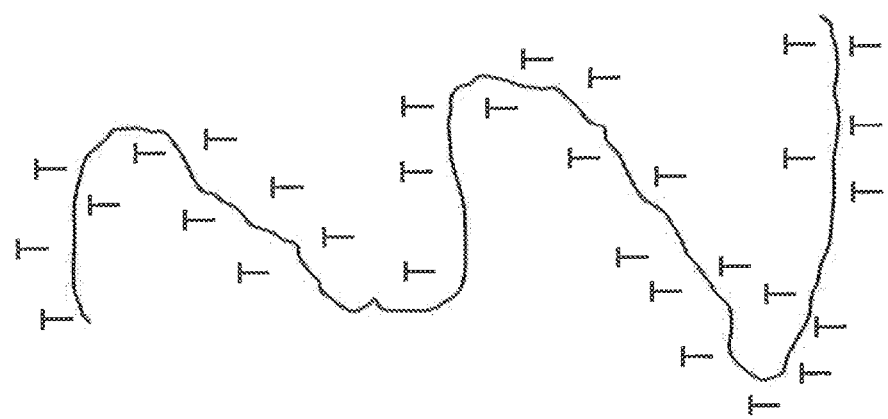
Figure 4D:
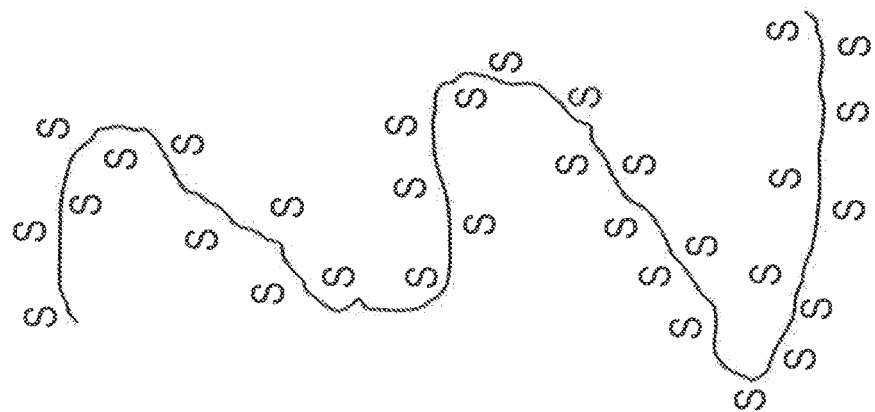

FIGS. 4D, 4E and 4F show the molecular structure of the biomarkers of FIGS. 4A-4C in a medium that includes the surfactant sodium dodecyl sulfate. As shown in these figures, the ionic bonds are broken, thereby causing the structures to relax or unfurl. This effect allows the fluorophore to be more accessible for detection by a light detector.

The invention is further illustrated by the examples provided below, which are directed to certain embodiments of the invention and are not intended to limit the full scope of the invention as set forth in the appended claims.

EXAMPLES

Several media were prepared using different surfactants and biomarkers for comparison purposes. The media contained from 0% to 5% surfactant, comparative amounts of selected biomarkers, and a buffering solution. The biomarkers used were a 150 kDa carboxy methyl dextran conjugated to Texas Red, FITC and 2SHR, respectively, and a 5 kDa carboxy methyl dextran conjugated to FITC. The test results are shown in FIGS. 1-3 as explained more fully below.

FIG. 1 shows the results of adding a 1% solution of sodium dodecyl sulfate to a media containing a 150 kDa carboxy methyl dextran conjugated to Texas Red, FITC and 2SHR, respectively. The fluorescent values recorded for these samples, which included 1% sodium dodecyl sulfate, were normalized to samples which did not include sodium dodecyl sulfate. As shown, the addition of sodium dodecyl sulfate to the media resulted in a comparatively small increase in the amount of fluorescence generated by the dextran-FITC conjugate. However, the dextran-TR conjugate experienced a 2-fold increase, while the dextran-2SHR conjugate experienced a 5-fold increase.

Figure 2:
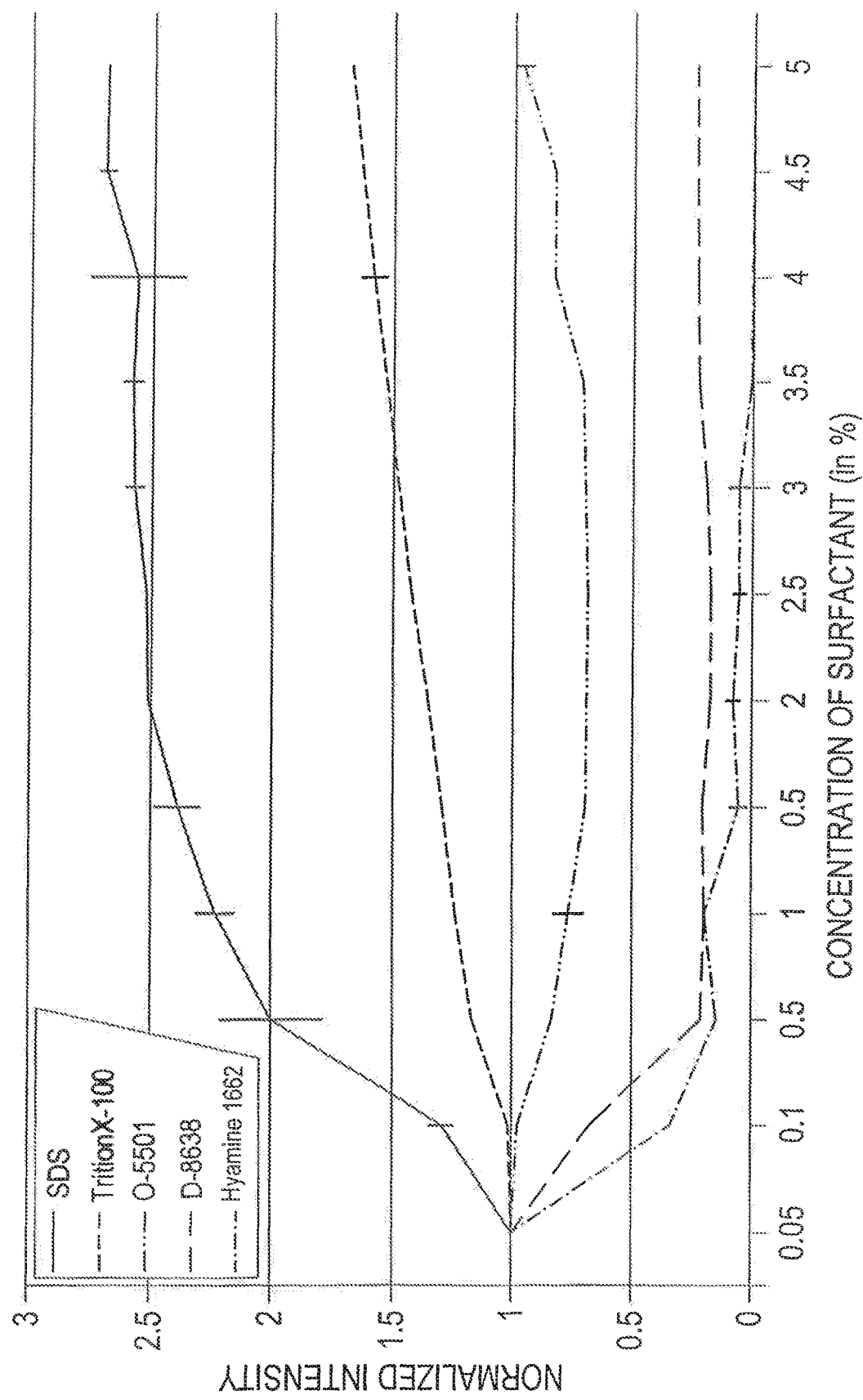
FIG. 2 is a graph showing the effect of various surfactants on the fluorescence of 2SHR conjugated to a 150 kDa carboxy methyl dextran.

FIG. 2 shows the results of the addition of various surfactants on the fluorescent emissions of normalized 150 kDa carboxy methyl dextran conjugated to 2SHR in canine plasma. The surfactants evaluated were as follows: O-5501 or oxyphenonium bromide, a cationic surfactant; Hyamine 1622, a cationic surfactant; D-8638 or dodecyltrimethylammonium bromide, a cationic surfactant; Triton X-100, a non-ionic surfactant; and SDS, an anionic surfactant. SDS produced the greatest increase in fluorescence, plateauing at about a 2.5 fold increase at concentrations greater than 1.5% surfactant.

Figure 3:
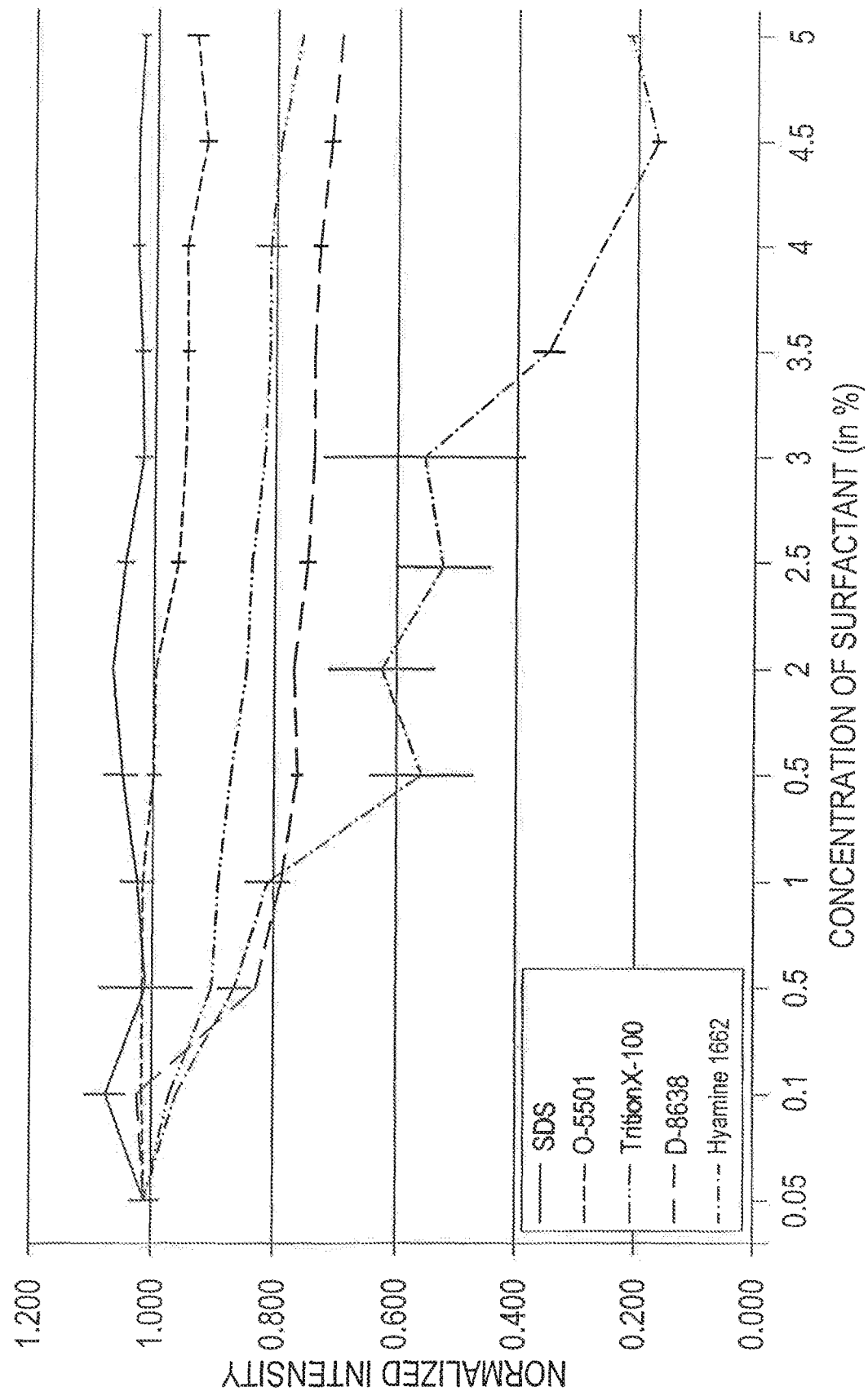
FIG. 3 is a graph showing the effect of various surfactants on the fluorescence of FITC conjugated to a 5 kDa carboxy methyl dextran.

FIG. 3 shows the effects of various surfactants on the fluorescence of normalized 5 kDa carboxy methyl dextran conjugated to FITC in canine plasma. SDS produced the least change in fluorescence of this biomarker at all concentration ranges. The other surfactants, with the exception of SDS, caused a decrease in fluorescence with increasing surfactant concentration.

Figure 5:
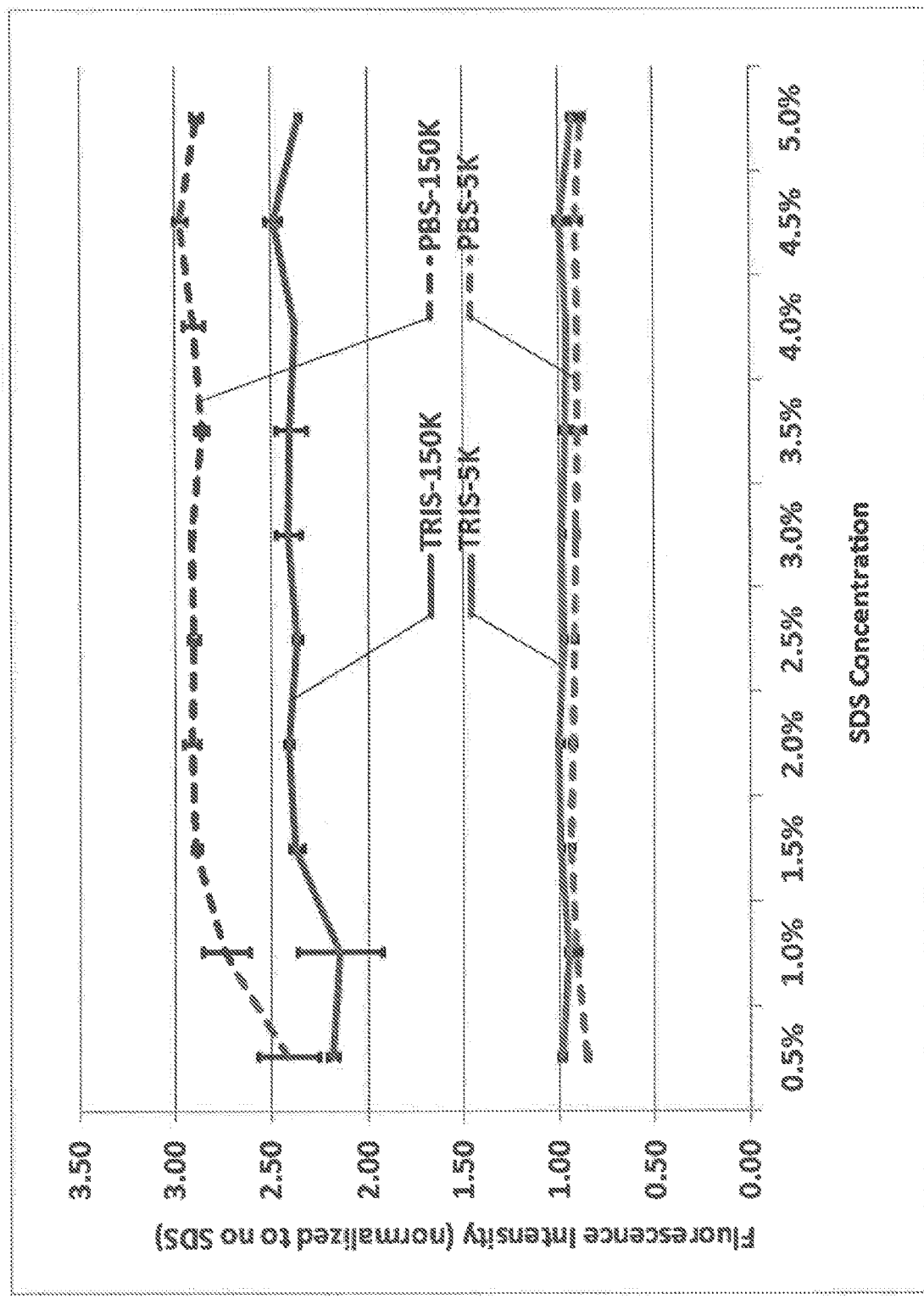
FIG. 5 is a graph showing the effect buffer on the fluorescence of 2SHR conjugated to a 150 kDa carboxy methyl dextran in the presence of varying amounts of SDS.

FIG. 5 shows the results of the comparison of TRIS and PBS buffering solutions on the fluorescent emissions of normalized 5 kDa and 150 kDa carboxy methyl dextran conjugated to 2SHR in canine plasma in the presence of varying amounts of SDS. PBS was found to increase the fluorescence of 2SHR 150 kDa more than TRIS.

The significance of the above results is as follows. An ideal surfactant for use in an in vitro assay to determine plasma volume, would cause an enhancement of the fluorescent signal generated by a large molecular weight biomarker. This biomarker would be expected to remain relatively constant in plasma.

However, the fluorescent signal generated by a small molecular weight biomarker whose concentration would be expected to decay as a function of time, such as glomerular filtration rate (GFR), should remain as strong as possible, or preferably unaffected, to assist detection. It is noteworthy that SDS did not affect the fluorescence of the small molecular weight marker. This is an important consideration for the accurate detection of the concentration of small markers for GFR determination, particularly for plasma samples taken at later time points where biomarker concentrations would be expected to be low.

Summarizing, the above results demonstrate that SDS is a suitable anionic surfactant for increasing the detection of fluorescent signals from biomarkers used for the measurement of physiological parameters of interest.

While the invention has been illustrated and described in detail in the drawings and foregoing description, this is to be considered as illustrative and not restrictive in character. It is understood that one of ordinary skill in the art could readily make changes and modifications to the above-described embodiments and that it would be impractical to attempt to describe all such embodiment variations in the present specification. Accordingly, it is understood that all such changes and modifications that come within the spirit of the invention are desired to be protected.

What is claimed is:

1. A composition for increasing fluorescent signals generated by a biological marker used for the diagnosis of a physiological condition, said composition comprising, in admixture,
   a buffering solution,
   a biological marker comprising at least one charged fluorescent molecule conjugated to dextran, said dextran having a molecular weight in the range from 70 kDa to 500 kDa, and
   an anionic surfactant comprising a negative charge.

2. The composition of claim 1, wherein the dextran is an anionic dextran.

3. The composition of claim 2, wherein the anionic dextran is conjugated to one or more cationically charged fluorophores.

4. The composition of claim 3, wherein the cationically charged fluorophore is 2 sulfhydrorhodamine (2SHR).

5. The composition of claim 1, wherein the anionic surfactant is sodium dodecyl sulphate (SDS).

6. The composition of claim 1, wherein the buffering solution is PBS.

7. The composition of claim 1, wherein said physiological condition being measured is either an organ function or a plasma volume.

8. A method for analyzing a biometric parameter in an animal comprising
   isolating a plasma sample from periodic samples of blood from an animal in whose vascular system a biological marker comprising at least one charged fluorescent molecule conjugated to dextran, said dextran having a molecular weight in the range from 70 kDa to 500 kDa, has been administered, and the biological marker allowed to reach equilibrium concentration in the vascular system,
      forming a medium for analysis, said medium comprising the plasma sample, a buffering solution and an anionic surfactant comprising a negative charge,
      subjecting the medium to a light source to activate the at least one fluorescent molecule,
      measuring and quantifying fluorescent signals generated by the at least one activated fluorescent molecule in presence of said anionic surfactant,
      comparing the quantity of the fluorescent signal(s) to the quantity from a control sample for a biometric parameter of the organ or tissue of the animal; and
   wherein the biometric parameter is the measurement of kidney function or plasma volume.

9. The method of claim 8, wherein the measurement of kidney function is glomerular filtration rate.

10. The method of claim 8, wherein the dextran is an anionic dextran.

11. The method of claim 10, wherein the anionic dextran is conjugated to one or more cationically charged fluorophores.

12. The method of claim 11, wherein the cationically charged fluorophore is 2 sulfhydrorhodamine (2SHR).

13. The method of claim 8, wherein the anionic surfactant is sodium dodecyl sulphate (SDS).

14. The method of claim 8, wherein the buffering solution is PBS.

15. The method of claim 8, wherein the biological marker is administered by intravenous injection.

16. The method of claim 8, wherein the signal is increased at least about 2-fold as compared to signal in the absence of anionic surfactant.

17. A method for increasing fluorescent signal of a biological marker comprising
   providing a biological sample containing a biological marker wherein the biological marker comprises at least one charged fluorescent molecule conjugated to dextran, said dextran having a molecular weight in the range from 70 kDa to 500 kDa; and
   adding a buffer solution and an anionic surfactant, said anionic surfactant, comprising a negative charge to said sample.

* * * * *